United States Patent [19]
Leiner

[11] Patent Number: 4,964,710
[45] Date of Patent: Oct. 23, 1990

[54] DISPOSABLE RIGID ENDOSCOPE

[76] Inventor: Dennis C. Leiner, 226 River St., Jaffrey, N.H. 03452

[21] Appl. No.: 385,388

[22] Filed: Jul. 27, 1989

[51] Int. Cl.$^5$ .......................... G02B 7/02; G02B 23/00
[52] U.S. Cl. ..................................... 350/572; 350/255
[58] Field of Search .............. 350/572, 573, 574, 575, 350/96.26, 255, 252; 128/4, 5, 6, 7, 8, 9

[56] References Cited
U.S. PATENT DOCUMENTS 3,807,836  4/1974  Baker ................................. 350/470
4,036,218  7/1977  Yamashita et al. ................. 350/573
4,784,118  11/1988  Fantone et al. ..................... 350/252

Primary Examiner—Bruce Y. Arnold
Assistant Examiner—Tho V. Tran

[57] ABSTRACT

An endoscope is provided with an objective lens system, an ocular lens and an intermediate relay lens system. The relay lens system is a hybrid system using both plastic and glass elements. The plastic elements comprise an even plurality (N) of axially aligned lenses each having a length of the same order as its diameter. Intermediate said plastic lenses are a plurality (N minus 1) of axially aligned glass plano cylinder, the end faces of which are polished.

7 Claims, 1 Drawing Sheet

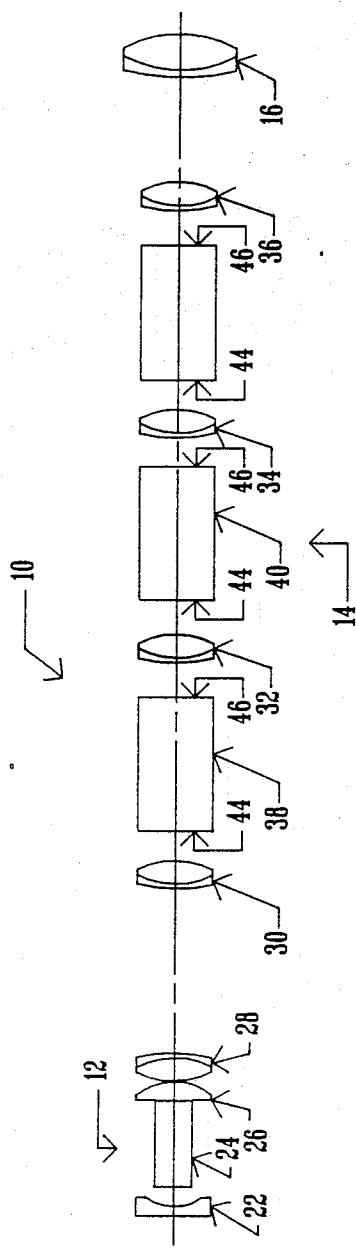

DISPOSABLE RIGID ENDOSCOPE

BACKGROUND OF THE INVENTION

This invention relates generally to disposable rigid endoscopes for use in viewing a region within a body cavity. Endoscopes are optical instruments which are well known in the art, and are very useful in permitting the examination of body cavities without the need for extensive surgery.

Currently used rigid endoscopes are comprised of many optical lenses mounted in a tube to relay an image from inside a body cavity for viewing by a physician in order to diagnose various diseases or conditions. Since presently used lenses are made of glass that is ground and polished by conventional techniques, the cost of these instruments precludes disposing of the instrument after each surgery. Physicians desire to dispose of these instruments after each surgery to eliminate the risk of exposing the next patient to diseases such as AIDS or hepatitis. While most surgical instruments can be sterilized with high pressure steam, the delicate nature of the endoscope makes such sterilization difficult. Also, because of the fragility of these instruments, they are frequently broken, at great cost to the user.

A conventional endoscope includes a pipe for illuminating the region of the body to be viewed, and a lens system for focusing and relaying the image of the illuminated object. There are a number of disadvantages to prior art endoscopes which this and previous inventions have sought to overcome.

Referring specifically to U.S. Pat. Nos. 3,089,484 to Hett, 3,257,902 to Hopkins, 3,556,085 to Takahashi, 4,267,828 to Matsuo and 4,273,110 to Groux, Fantone, in his U.S. Pat. No. 4,784,118, pointed out that the prior art endoscope were complex and expensive to manufacture because of the use of carefully ground glass lenses. Fantone indicated that because of the high cost of glass lenses, endoscopes could not be made inexpensively, and therefore, disposable. In order to reduce the cost and complexity of the prior art systems, Fantone constructed an endoscope in which the light pipe, and the objective, relay, and viewing lens assemblies were all made of a polymeric material which lent themselves to injection molding. Such materials included acrylics, polystyrenes, polycarbonates and styrene-acrylonitrile (SAN) copolymers.

While the Fantone endoscope had some advantages over the prior art, the device had several problems. First, the plastic relay lenses were composed of only one material which increases the chromatic aberration of the image and reduces the resolution. In addition, in order to obtain a bright image, the plastic lenses have to be much longer than their diameters, and this is very difficult to manufacture using currently known manufacturing techniques.

To overcome these problems, I employ a hybrid system which incorporates glass plano cylinders disposed between molded plastic curved surface lenses which have a thickness on the same order of magnitude as their diameter. The plastic lenses can be made of two different types of plastic to allow for the correction of chromatic aberration. In order to achieve a bright image, the plano glass cylinders with flat polished end faces are placed in between the plastic lenses. In contrast to ground and polished lenses, the plano glass cylinders can be economically made in large quantities, while the smaller plastic lenses can be economically and accurately made by known injection molding processes. Therefore, my invention overcomes the major deficiencies of the prior art, while permitting the manufacture of a low cost, disposable endoscope.

SUMMARY OF THE INVENTION

It is a primary object of this invention to provide an endoscope comprising a hybrid system of lenses using a combination of polished glass and molded plastic elements.

It is another object of this invention to provide a low cost, disposable endoscope which overcomes certain of the deficiencies of the prior art by using a hybrid comprised of glass plano rods interposed between curved surface molded plastic lenses.

Another object of this invention is to provide a disposable endoscope in which the relay viewing assemblies are comprised of a combination of glass and molded plastic optical elements.

For further objects and advantages of this invention, reference should now be made to the following detailed specification and to the accompanying drawing in which the single FIGURE depicts a diagrammatic representation of the invention.

DETAILED DESCRIPTION OF THE INVENTION

The single FIGURE of the drawing depicts a diagrammatic embodiment of the invention intended for incorporation in an endoscope similar to that shown in the previously mentioned Fantone Pat. No. 4,784,118. As in Fantone, the complete device would include an elongate light pipe and a source of light. This invention, and the accompanying description, is limited to the system of lenses including the objective lenses, the ocular lens and the relay lenses.

Referring to the drawing, endoscope 10 includes a conventional objective lens system 12 located at the distal end of the endoscope, a relay lens system 14 which includes my inventive improvement over the prior art, and a conventional ocular lens 16.

The objective lens system includes a field widening lens 22, a prism, depicted for simplicity as prism tunnel 24, and objective lenses 26 and 28. These elements, and the ocular lens 16 may be made of plastic, as taught by Fantone, or they may be made conventionally of glass.

The relay lens system comprises an even number (N) of axially aligned molded polymeric curved surface lenses 30, 32, 34 and 36, the lengths of these lenses being on the same order as their diameter, thereby resulting in ease and economy of manufacture. Optionally, the lenses 30 to 36 may be made of two different types of plastic material. In order to achieve a bright image, an odd number N minus 1 of plano glass cylinders 38, 40 and 42 with flat polished end faces 44 and 46 are placed in between the plastic lenses 30, 32, 34 and 36. In contrast to ground and polished lenses with curved surfaces, the plano glass cylinders can be economically made in large quantities and are thus suitable for use in a disposable endoscope. Unlike the Fantone plastic lens which is very difficult to make using current plastic injection molding techniques, the plastic lenses used in my hybrid system can be made with precision and with economy of manufacture. The combination of glass and plastic therefore achieves the desired results, namely, a precise and economical endoscope.

Various modifications and adaptations of my invention will become apparent to persons skilled in the art. It is intended therefore, that this invention be limited only by the following claims as interpreted in the light of the prior art.

I claim:

1. An endoscope for viewing an object, said apparatus including a relay lens assembly, said assembly including:
   a plurality of axially aligned polymeric curved surface, spaced lenses; and
   a plurality of axially aligned plano glass cylinders with polished end faces positioned intermediate said spaced lenses.

2. The invention as defined in claim 1 wherein said lenses have a length which is of the order of their diameter.

3. The invention as defined in claim 1 wherein said lenses are molded.

4. The invention as defined in claim 1 wherein said lenses are made of two different polymeric materials.

5. The invention as defined in claim 1 wherein said lenses have a length which is of the order of their diameter, and wherein said lenses are molded.

6. The invention as defined in claim 1 wherein said lenses have a length which is of the order of their diameter and wherein said lenses are molded, and wherein said lenses are made of two different polymeric materials.

7. The invention as defined in claim 1 wherein said plurality of lenses is an even number (N), and wherein said plurality of cylinders is an odd number (N minus 1).

* * * * *

REEXAMINATION CERTIFICATE (2356th)
United States Patent [19]
Leiner

[11] B1 4,964,710
[45] Certificate Issued Aug. 16, 1994

[54] DISPOSABLE RIGID ENDOSCOPE

[75] Inventor: Dennis C. Leiner, Jaffrey, N.H.

[73] Assignee: Monadnock Optics, Inc., Huntington Valley, Pa.

Reexamination Request:
No. 90/003,203, Sep. 23, 1993

Reexamination Certificate for:
Patent No.: 4,964,710
Issued: Oct. 23, 1990
Appl. No.: 385,388
Filed: Jul. 27, 1989

[51] Int. Cl.$^5$ .................. G02B 7/02; G02B 23/00
[52] U.S. Cl. .................. 359/434; 359/435; 359/503; 359/504; 359/819; 359/823; 385/117; 128/4; 128/5; 128/6; 128/7; 128/8; 128/9
[58] Field of Search ............... 359/435, 434, 793, 795

[56] References Cited
U.S. PATENT DOCUMENTS

| | | |
|---|---|---|
| 3,089,484 | 5/1963 | Hett . |
| 3,257,902 | 6/1966 | Hopkins . |
| 3,556,085 | 1/1971 | Takahashi . |
| 4,025,155 | 5/1977 | Imai . |
| 4,148,550 | 4/1979 | MacAnally . |
| 4,148,551 | 4/1979 | MacAnally . |
| 4,168,882 | 9/1979 | Hopkins . |
| 4,267,828 | 5/1981 | Matsuo . |
| 4,273,110 | 6/1981 | Groux . |
| 4,300,812 | 11/1981 | Nakahashi . |
| 4,385,810 | 5/1983 | Hamou . |
| 4,545,652 | 10/1985 | Hoogland . |
| 4,575,195 | 3/1986 | Hoogland . |
| 4,704,007 | 11/1987 | Landre et al. . |
| 4,723,843 | 2/1988 | Zobel . |
| 4,946,267 | 8/1990 | Hoogland . |
| 4,969,708 | 11/1990 | Leiner . |
| 4,993,817 | 2/1991 | Hoogland . |
| 5,005,960 | 4/1991 | Heimbeck . |

FOREIGN PATENT DOCUMENTS

| | | |
|---|---|---|
| 3838168 | 5/1989 | Fed. Rep. of Germany . |
| 544422 | 3/1977 | U.S.S.R. . |
| 686725 | 2/1979 | U.S.S.R. . |
| 683721 | 9/1979 | U.S.S.R. . |

OTHER PUBLICATIONS

The Handbook Of Plastic Optics, Chapter 5, "Optical Design", pp. 57–93 (2nd Ed. 1983).
Modern Optical Engineering, The Design Of Optical Systems, 1966, Section 7.5, pp. 159–160.

*Primary Examiner*—Jon W. Henry

[57] ABSTRACT

An endoscope is provided with an objective lens system, and ocular lens and an intermediate relay lens system. The relay lens system is a hybrid system using both plastic and glass elements. The plastic elements comprise an even plurality (N) of axially aligned lenses each having a length of the same order as its diameter. Intermediate said plastic lenses are a plurality (N minus 1) of axially aligned glass plano cylinder, the end faces of which are polished.

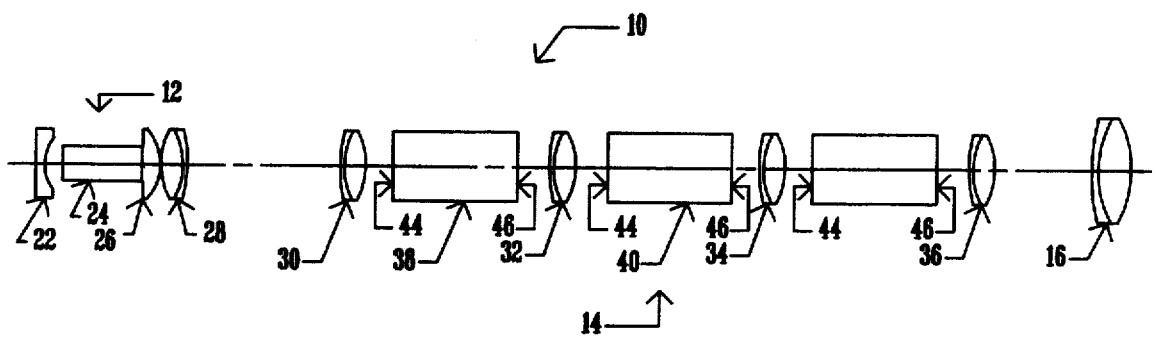

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 2, 3, 5, 6 and 7, dependent on an amended claim, are determined to be patentable.

New claims 8-18 are added and determined to be patentable.

1. An endoscope for viewing an object, said [apparatus] *endoscope* including a relay lens assembly, said assembly including:
   a plurality of axially aligned polymeric curved surface spaced lenses; and
   a plurality of axially aligned plano glass cylinders with polished end faces positioned intermediate said spaced lenses *and not intermediate curved surface glass lenses*.

4. [The invention as defined in claim 1] *An endoscope for viewing an object, said endoscope including a relay lens asssembly, said assembly including:*
   *a plurality of axially aligned polymeric curved surface spaced lenses; and*
   *a plurality of axially aligned plano glass cylinders with polished end faces positioned intermediate said spaces lenses,* wherein said lenses are made of two different polymeric materials.

8. *The invention as defined in claim 4 wherein said lenses have a length which is of the order of their diameter.*

9. *The invention as defined in claim 4 wherein said lenses are molded.*

10. *The invention as defined in claim 4 wherein said plurality of lenses is an even number (N), and wherein said plurality of cylinders is an odd number (N minus 1).*

11. *An endoscope for viewing an object, said endoscope including a relay lens assembly without curved surface glass lenses, said assembly including:*
    *a plurality of axially aligned polymeric curved surface spaced lenses; and*
    *a plurality of axially aligned plano glass cylinders with polished end faces positioned intermediate said spaced lenses.*

12. *The invention as defined in claim 11 wherein said lenses have a length which is of the order of their diameter.*

13. *The invention as defined in claim 11 wherein said lenses are molded.*

14. *The invention as defined in claim 11 wherein said plurality of lenses is an even number (N), and said plurality of cylinders is an odd number (N minus 1).*

15. *An endoscope for viewing an object, said endoscope including a relay lens assembly, said assembly consisting essentially of:*
    *a plurality of axially aligned polymeric curved surface spaced lenses; and*
    *a plurality of axially aligned plano glass cylinders with polished end faces positioned intermediate said spaced lenses.*

16. *The invention as defined in claim 15 wherein said lenses have a length which is of the order of their diameter.*

17. *The invention as defined in claim 15 wherein said lenses are molded.*

18. *The invention as defined in claim 15 wherein said plurality of lenses is an even number (N), and said plurality of cylinders is an odd number (N minus 1).*

* * * * *